United States Patent
Kilcher et al.

(10) Patent No.: US 9,452,027 B2
(45) Date of Patent: Sep. 27, 2016

(54) DENTAL COMPOSITE APPLICATOR AND RELATED METHODS

(75) Inventors: Beat Kilcher, Bosco Luganese (CH); Marco Da Rold, Odogno (CH)

(73) Assignee: KerrHawe SA, Bioggio (CH)

( * ) Notice: Subject to any disclaimer, the term of this patent is extended or adjusted under 35 U.S.C. 154(b) by 1628 days.

(21) Appl. No.: 12/634,986

(22) Filed: Dec. 10, 2009

(65) Prior Publication Data

US 2011/0143303 A1    Jun. 16, 2011

(51) Int. Cl.
  *A61C 3/08*  (2006.01)
  *A61C 1/07*  (2006.01)
  *A61C 5/06*  (2006.01)

(52) U.S. Cl.
  CPC . *A61C 3/08* (2013.01); *A61C 1/07* (2013.01); *A61C 5/062* (2013.01)

(58) Field of Classification Search
  CPC ........... A61C 3/08; A61C 1/07; A61C 5/062
  USPC ................ 433/25, 27, 80–90, 114, 118–119, 433/141–147
  See application file for complete search history.

(56) References Cited

U.S. PATENT DOCUMENTS

| | | |
|---|---|---|
| 823,150 A | 6/1906 | Alexander |
| 3,763,411 A | 10/1973 | Goof |
| 3,809,977 A | 5/1974 | Balamuth et al. |
| 3,890,713 A | 6/1975 | Nielsen |
| 3,914,868 A | 10/1975 | Schwartz et al. |
| 4,092,778 A | 6/1978 | Hirdes |
| 4,173,828 A | 11/1979 | Lustig et al. |
| 4,371,816 A | 2/1983 | Wieser |
| 4,718,851 A | 1/1988 | Kuhn |
| 4,820,152 A | 4/1989 | Warrin et al. |
| 4,850,875 A | 7/1989 | Takatsu |
| 4,880,382 A | 11/1989 | Moret et al. |
| 4,913,133 A | 4/1990 | Tichy |
| 4,963,095 A | 10/1990 | Weissman |
| 4,991,249 A | 2/1991 | Suroff |
| 4,992,048 A | 2/1991 | Goof |

(Continued)

FOREIGN PATENT DOCUMENTS

| | | |
|---|---|---|
| DE | 19736236 A1 | 7/1998 |
| DE | 10001513 A1 | 4/2001 |

(Continued)

OTHER PUBLICATIONS

Hu-Friedy, "Composit/Plastic Filling Instruments," Hu-Friedy Website, downloaded Jul. 27, 2010, 11pp. (http://www.hu-friedy.com/product/itemGroup.aspx?CategoryIndex=0&CategoryID=Restorative&GroupIndex=0&GroupID=PLF&ItemsPerPage=99&PageIndex=0).

(Continued)

*Primary Examiner* — Edward Moran
(74) *Attorney, Agent, or Firm* — Wood, Herron & Evans, LLP

(57) ABSTRACT

A vibrating applicator is provided for applying a dental composite material onto a tooth. The applicator has an elongated body and a tip that is coupled to the elongated body to apply the dental composite material onto the tooth. The applicator further has a vibrating apparatus for vibrating the tip and a sensor for sensing a condition of the dental composite material. A controller is operatively coupled to the vibrating apparatus and to the sensor and is configured to automatically vary an output frequency of the vibrating apparatus in response to the condition sensed by the sensor.

27 Claims, 2 Drawing Sheets

(56) References Cited

U.S. PATENT DOCUMENTS

| | | | |
|---|---|---|---|
| 5,002,487 A | 3/1991 | Tichy | |
| 5,044,356 A | 9/1991 | Fishman et al. | |
| 5,133,661 A | 7/1992 | Euvrard | |
| 5,145,369 A | 9/1992 | Lustig et al. | |
| 5,151,030 A | 9/1992 | Comeaux | |
| 5,158,457 A | 10/1992 | Meier et al. | |
| 5,318,445 A | 6/1994 | Meier et al. | |
| 5,340,310 A | 8/1994 | Bifulk | |
| 5,382,162 A | 1/1995 | Sharp | |
| 5,639,238 A | 6/1997 | Fishburne, Jr. | |
| 5,725,370 A | 3/1998 | Himeno et al. | |
| 5,797,747 A | 8/1998 | Badoz et al. | |
| 5,839,895 A | 11/1998 | Fishburne, Jr. | |
| 5,915,965 A | 6/1999 | Ohlsson et al. | |
| 5,924,864 A | 7/1999 | Loge et al. | |
| 5,931,672 A | 8/1999 | Postal et al. | |
| 5,947,728 A | 9/1999 | Riebl et al. | |
| 5,971,758 A | 10/1999 | Hugo et al. | |
| 5,997,172 A | 12/1999 | Wakabayashi | |
| 6,106,289 A | 8/2000 | Rainey et al. | |
| 6,224,379 B1 | 5/2001 | Abedian et al. | |
| 6,227,853 B1 | 5/2001 | Hansen et al. | |
| 6,247,931 B1 | 6/2001 | Postal et al. | |
| 6,267,594 B1 | 7/2001 | Hugo | |
| 6,269,686 B1* | 8/2001 | Hahn et al. | 73/54.24 |
| 6,273,717 B1 | 8/2001 | Hahn et al. | |
| 6,488,500 B2 | 12/2002 | Rosenstatter | |
| 6,545,390 B1 | 4/2003 | Hahn et al. | |
| 6,602,073 B2 | 8/2003 | Schilling et al. | |
| 6,716,028 B2 | 4/2004 | Rahman et al. | |
| 6,722,882 B2 | 4/2004 | Buchanan | |
| 6,752,629 B2 | 6/2004 | Suzuki et al. | |
| 6,811,399 B2 | 11/2004 | Rahman et al. | |
| 6,910,887 B2 | 6/2005 | Van Den Houdt | |
| 6,955,539 B2 | 10/2005 | Shortt et al. | |
| 7,011,520 B2 | 3/2006 | Rahman et al. | |
| 7,014,462 B1 | 3/2006 | Tilse | |
| 7,044,736 B2 | 5/2006 | Atkin et al. | |
| 7,217,128 B2 | 5/2007 | Atkin et al. | |
| 7,254,858 B2 | 8/2007 | Hafliger et al. | |
| 7,261,561 B2 | 8/2007 | Ruddle et al. | |
| 7,455,521 B2 | 11/2008 | Fishburne, Jr. | |
| 2002/0123703 A1 | 9/2002 | Mark | |
| 2003/0134255 A1 | 7/2003 | Masterman et al. | |
| 2003/0162145 A1 | 8/2003 | Masterman et al. | |
| 2005/0026106 A1 | 2/2005 | Jefferies | |
| 2005/0037316 A1* | 2/2005 | Sholder | 433/119 |
| 2005/0142515 A1 | 6/2005 | Levy et al. | |
| 2006/0269900 A1* | 11/2006 | Paschke et al. | 433/119 |
| 2007/0054240 A1 | 3/2007 | Masterman et al. | |
| 2007/0190485 A1* | 8/2007 | Hayman et al. | 433/118 |
| 2007/0224575 A1 | 9/2007 | Dieras et al. | |
| 2007/0231772 A1 | 10/2007 | Jefferies | |
| 2008/0014552 A1 | 1/2008 | Masterman et al. | |
| 2008/0064006 A1* | 3/2008 | Quan et al. | 433/119 |
| 2008/0206706 A1* | 8/2008 | Mossle | 433/118 |
| 2008/0213731 A1 | 9/2008 | Fishburne | |
| 2008/0318184 A1 | 12/2008 | Zargari | |
| 2009/0142729 A1 | 6/2009 | Neumeyer | |
| 2010/0035203 A1 | 2/2010 | Moessle | |
| 2010/0036535 A1* | 2/2010 | Feine et al. | 700/282 |

FOREIGN PATENT DOCUMENTS

| | | |
|---|---|---|
| DE | 19952801 A1 | 5/2001 |
| DE | 102005058879 A1 | 6/2007 |
| DE | 102007022205 A1 | 11/2008 |
| DE | 102007052442 A1 | 5/2009 |
| EP | 0535542 B1 | 6/1995 |
| EP | 0868887 A2 | 10/1998 |
| EP | 1145687 A1 | 10/2001 |
| EP | 1880689 A1 | 1/2008 |
| EP | 2008614 A1 | 12/2008 |
| EP | 2042121 A1 | 4/2009 |
| EP | 2055257 A2 | 5/2009 |
| GB | 2269105 A | 2/1994 |
| JP | 2008125613 A | 6/2008 |
| WO | 9831295 A1 | 7/1998 |
| WO | 9908617 A1 | 2/1999 |
| WO | 2004071326 A1 | 8/2004 |
| WO | 2004073538 A2 | 9/2004 |
| WO | 2006034133 A1 | 3/2006 |
| WO | 2006034281 A1 | 3/2006 |
| WO | 2006044099 A1 | 4/2006 |
| WO | 2007014548 A2 | 2/2007 |
| WO | 2008092482 A1 | 8/2008 |
| WO | 2008122386 A1 | 10/2008 |
| WO | 2008138545 A2 | 11/2008 |
| WO | 2009056126 A2 | 5/2009 |
| WO | 2009113843 A1 | 9/2009 |

OTHER PUBLICATIONS

European Patent Office, Search Report and Preliminary Opinion issued in corresponding European Application No. 10191944.7 dated Mar. 28, 2011, 6 pp.

* cited by examiner

DENTAL COMPOSITE APPLICATOR AND RELATED METHODS

TECHNICAL FIELD

This invention relates generally to dental instruments and, more particularly, to vibrating applicators applying a dental composite material onto a tooth.

BACKGROUND

Instruments are known for applying a dental composite material onto a tooth. A disadvantage of composite materials, however, is their tendency to adhere more or less to the instrument that is used to apply or shape them. As a result, and by way of example, the composite material has a tendency to be drawn off from the edges of the cavity, to be distributed inhomogeneously on the tooth surface, and to form air bubbles during the distribution.

To this end, instruments have been developed that address the challenges observed in the application of composite materials. For example, known instruments may include coatings such as TiN, or Teflon™, for example, on the working tip of the instrument to minimize the likelihood of the composite material adhering to the tip. Other instruments may include a vibrating tip. In instruments of this type, however, the tip may vibrate at a fixed frequency and/or amplitude, in which case the material adheres to the tip when the viscosity of the material reaches a predetermined level, characteristic of the particular material. For example, an instrument may apply a composite material with a predetermined, fixed output frequency of vibration. Initially, the viscosity of the material is reduced to an acceptable level by virtue of engagement of the instrument with the material. After a predetermined length of time of engagement, however, the viscosity of the material may reach a level at which the material adheres to the tip of the instrument, which is undesirable. The user may then be forced to clean or replace the instrument altogether. Similarly, for a predetermined output frequency of vibration, there may be a difference in the viscosity level of the composite material according to the depth of insertion of the tip of the instrument into the material, which may also result in adhesion of portions of the material having a particular level of viscosity.

It is therefore desirable to provide a dental instrument that addresses these and other problems associated with conventional instruments used to apply a dental composite material onto a tooth.

SUMMARY

The present invention overcomes the foregoing and other shortcomings and drawbacks of applicators heretofore known for applying a dental composite material onto a tooth. While the invention will be discussed in connection with certain embodiments, it will be understood that the invention is not limited to these embodiments. On the contrary, the invention includes all alternatives, modifications, and equivalents as may be included within the scope of the invention.

In one embodiment, an applicator is provided for applying a dental composite material onto a tooth. The applicator has an elongated body and a tip that is coupled to the elongated body to apply the dental composite material onto the tooth. The applicator further has a vibrating apparatus for vibrating the tip and a sensor for sensing a condition of the dental composite material. A controller is operatively coupled to the vibrating apparatus and to the sensor and is configured to automatically vary an output frequency of the vibrating apparatus in response to the condition sensed by the sensor. In a specific embodiment, the sensor is configured to sense a viscosity of the dental composite material. The sensor may, for example, be configured to sense a force exerted by the dental composite material on the tip.

The controller may be configured to decrease the output frequency in response to a sensed decrease in the force exerted by the dental composite material on the tip. Additionally or alternatively, the controller may be configured to increase the output frequency in response to a sensed increase in the force exerted by the dental composite material on the tip. In a specific embodiment, the elongated body defines a longitudinal axis of the applicator, with the sensor being configured to sense a force exerted by the dental composite on the tip that is orthogonal to the longitudinal axis of the applicator. Additionally or alternatively, the sensor may be configured to sense a force exerted by the dental composite on the tip that is generally parallel to or along the longitudinal axis. Additionally or alternatively, the controller may have a plurality of predetermined algorithms of operation, with each of the algorithms defining a specific relationship between the sensed condition and the output frequency.

The vibrating apparatus may be operable to vibrate the tip with an output frequency in the range of about 80 Hz to about 500 Hz. The vibrating apparatus may, additionally or alternatively, be operable to vibrate the tip with an output amplitude in the range of about 0.1 mm to about 0.5 mm. In one specific embodiment, the tip is generally spherical, with the vibrating apparatus being operable to vibrate the generally spherical tip with a frequency in the range of about 100 Hz to about 500 Hz. The vibrating apparatus may be operable to vibrate the generally spherical tip with an amplitude of about 0.05 mm. The tip may be releasably coupled to the elongate body to thereby permit replacement thereof with another tip.

The applicator, in a specific embodiment, is powered by a battery, with the applicator also having a compartment in the elongated body for receiving the battery therein. The tip may include one of a brush or a rotatable portion configured to distribute the dental composite material on the tooth during vibration of the tip.

In another embodiment, an applicator is provided for applying a dental composite material onto a tooth. The applicator has a handle, and a plurality of tips that are each selectively configured for coupling to the handle to apply the dental composite material onto the tooth. A vibrating apparatus vibrates the coupled tip, and a sensor senses a viscosity of the dental composite material being applied to the tooth. A controller is operatively coupled to the vibrating apparatus and to the sensor and is configured to automatically vary an output frequency of the vibrating apparatus in response to the viscosity sensed by the sensor.

The sensor may, for example, be configured to sense a force exerted by the dental composite material on the coupled tip, with the controller being configured to automatically vary the output frequency in response to the force sensed by the sensor. The applicator may be such that the controller has a plurality of predetermined algorithms of operation, with each algorithm defining a specific relationship between the sensed viscosity and the output frequency.

In yet another embodiment, a method is provided for applying a dental composite material onto a tooth with an applicator having an applicator body, a tip that is coupled to the elongated body for applying the dental composite material, and a vibrating apparatus for vibrating the tip. The method includes vibrating the tip while applying the dental composite material onto the tooth and sensing a condition of the dental composite material engaged by the tip. An output frequency of the vibrating apparatus is automatically varied in response to the sensed condition of the dental composite material. In a specific embodiment, sensing a condition of the dental composite material includes sensing a viscosity thereof. In yet another specific embodiment, sensing a condition of the dental composite material includes sensing a force exerted by the dental composite material on the tip.

The method may include rotating a first portion of the tip relative to another portion thereof while vibrating the tip. The method may, additionally or alternatively, include vibrating the tip with a frequency in the range of about 80 Hz to about 100 Hz. The method may include decreasing or increasing the output frequency, respectively, in response to a sensed decrease or increase in the viscosity of the dental composite material. The method may include maintaining the output frequency such that it corresponds to a sensed force of about 0.2 N. The method may, additionally or alternatively, include selecting among a plurality of algorithms of operation of the applicator, with each of the algorithms defining a relationship between the sensed condition and the output frequency.

The above and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

Figure 1:
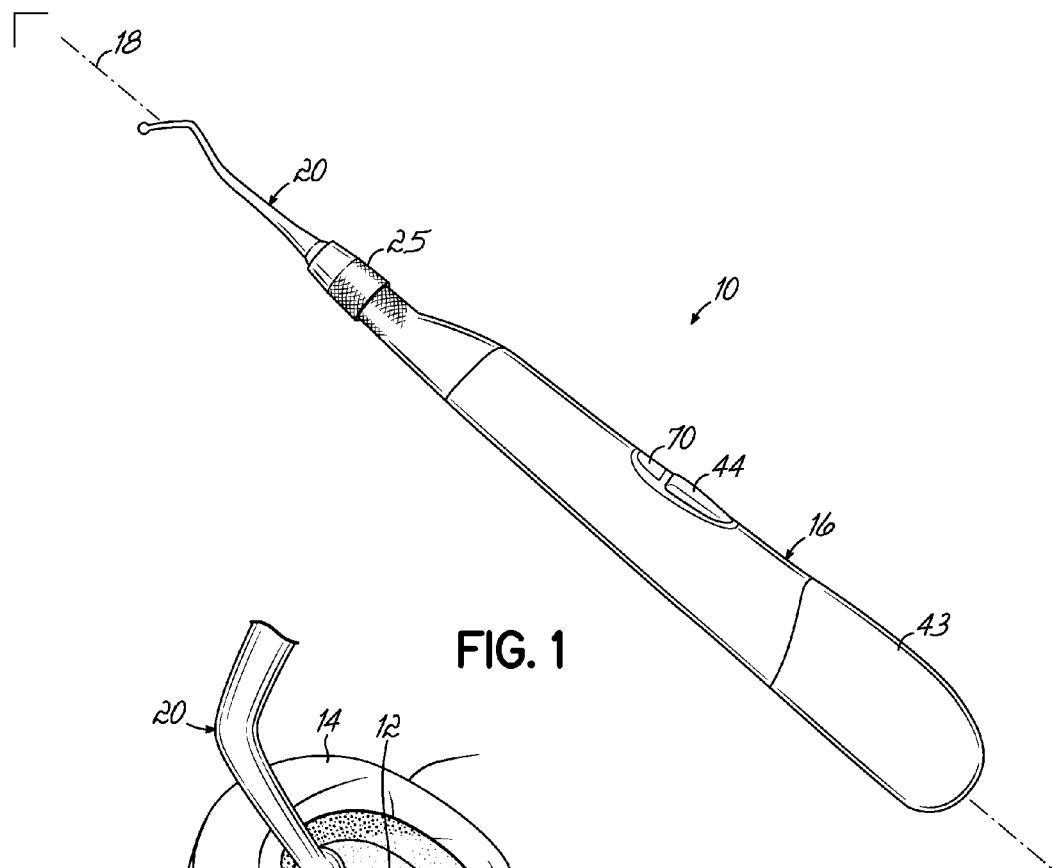
FIG. 1 is a perspective view of a dental applicator in accordance with one embodiment of the present invention.
Figure 2:
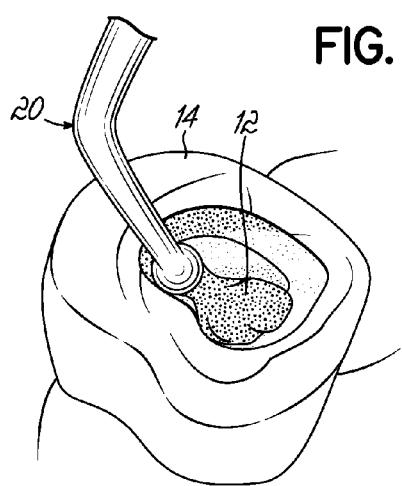
FIG. 2 is a perspective view illustrating an exemplary use of the applicator of FIG. 1.

With respect to the figures, and particularly to FIGS. 1-3 and 3A, an exemplary dental instrument in the form of an applicator 10 is illustrated for applying a dental composite material 12 onto a tooth 14, where the term "applying" generally includes shaping, smoothing or any other manipulation of the dental composite material 12 on the tooth 14. The applicator 10 includes an elongated body 16 defining a handle of the applicator 10, and extending generally along a longitudinal axis 18. A tip 20 is coupled to a longitudinal end of the elongated body 16 and is configured to apply the composite material 12 to the tooth 14 during vibration of the tip 20. To this end, the tip 20 may take one of many different forms. For example, and without limitation, the tip 20 may have a working end having a generally spherical shape (FIGS. 1, 2, and 4), a generally conical shape, a generally cylindrical shape, or any other suitably chosen shape.

Figure 3:
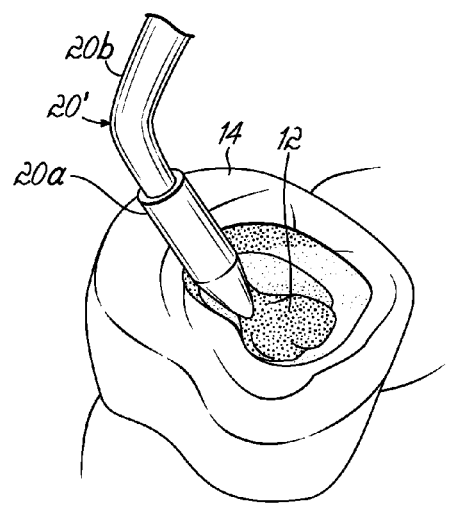
FIG. 3 is a view similar to FIG. 2 illustrating an alternative embodiment of a tip of the applicator of FIGS. 1-2.
Figure 3A:
FIG. 3A is a perspective view of yet another alternative embodiment of a tip of the applicator of FIGS. 1-2.

Moreover, as shown in FIG. 3A, a tip 20" may include a working end in the form of a brush configured to provide a smoothing function on the composite material 12 being applied to the tooth 14. Or it may alternatively or additionally be in the form of a rotatable tip 20' (FIG. 3), in which the tip 20' has an end portion 20a that is rotatable relative to a main portion 20b of the tip 20'. The tip 20 is made of a suitably chosen material such as, for example, stainless steel or a plastic material, and may have a coating made of titanium nitride (TiN) or polytetrafluoroethylene ("PTFE"), or it may have no coating at all. Exemplary tips suitable for use with the applicator 10 of the present disclosure are described in U.S. patent application Ser. No. 10/736,262, assigned to the assignee of the present application, and the disclosure of which is hereby expressly incorporated herein by reference in its entirety.

Figure 4:
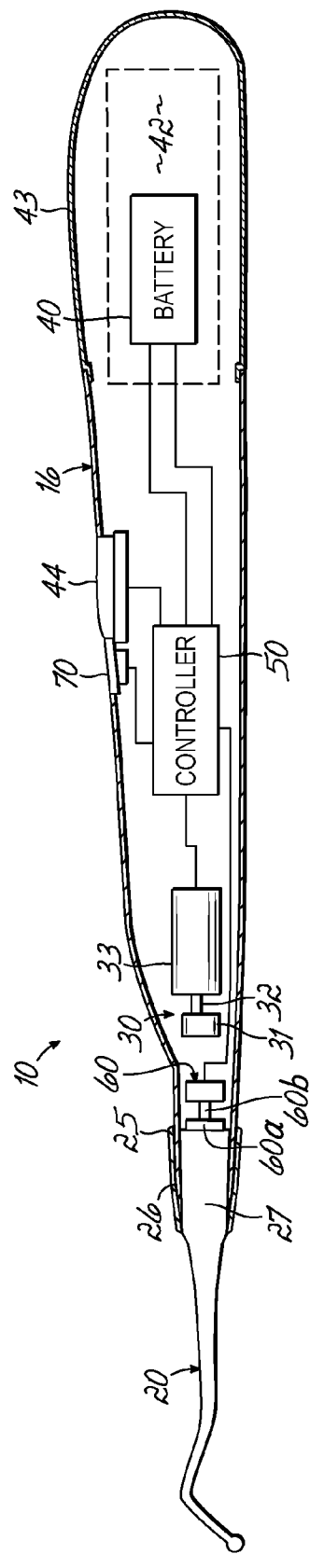
FIG. 4 is a schematic elevation view of the applicator of FIGS. 1-2.

In one aspect of the illustrated embodiment, and with further reference to FIG. 4, coupling between the tip 20 and elongated body 16 is releasable, such that the tip 20 may be readily interchanged with other tips, according to the particular needs of the user. To this end, releasable coupling between the tip 20 and elongated body 16 includes a rotatable chuck 25 that secures a plurality of prongs 26, which in turn grip a base 27 of tip 20. This type of coupling is exemplary rather than intended to be limiting, insofar as other types of coupling may be chosen instead and still fall within the scope of the present disclosure.

The tip 20 of the embodiment of the figures is vibratable. To this end, the applicator 10 includes a vibrating apparatus 30 within the elongated body 16 that is operatively coupled to the tip 20 to impart thereon an output vibrating frequency and an output vibrating amplitude. For example, and without limitation, the vibrating apparatus 30 may take the form of an eccentric element 31 driven by a shaft 32 that is, in turn, connected to a motor 33. In this regard, rotation of the shaft 32 causes rotation of the eccentric element 31 which, in turn, causes vibration of the elongated body 16. In such exemplary embodiment, vibration is transferred from the elongate body 16 to the tip 20, to thereby result in vibration of the tip 20. Those of ordinary skill in the art will readily appreciate that the above-described type of vibrating apparatus 30 and the components thereof are merely illustrative rather than intended to be limiting, insofar as the vibrating apparatus 30 may take other suitably chosen forms and still fall within the scope of the present disclosure.

With particular reference to FIGS. 1 and 4, the vibrating apparatus 30 is powered by a power supply, in this embodiment, in the form of a battery 40 that is housed within a battery compartment 42 located within the elongated body 16, and which is accessible through a cover 43. The battery 40 provides power to motor 33, which is, in turn, operatively coupled to the tip 20 through the vibrating apparatus 30. A switch 44, also located in the elongated body 16, selectively opens and closes a circuit (not shown), to thereby selectively energize and de-energize the vibrating apparatus 30. In this regard, an alternative contemplated use of the applicator 10 includes manipulating the tip 20 to apply the composite material 12 while the tip 20 is not vibrating (i.e., with switch 44 in an "off" position). Notably, the exemplary battery 40 powering applicator 10 makes the applicator 10 less cumbersome than conventional devices that use an external power supply. It is contemplated, however, that an alternative embodiment of the applicator 10 may have a different type of power supply, which may or may not be located within the elongated body 16.

Operation of the vibrating apparatus 30 is controlled by a controller 50 (schematically depicted in FIG. 4) to which the vibrating apparatus 30 is operatively coupled. The controller 50 may, in a specific embodiment, be located within the elongated body 16, although this is merely exemplary rather than intended to be limiting. The controller 50 controls the output frequency and the output amplitude of vibration of the tip 20. In a specific embodiment, the output frequency of vibration of vibrating apparatus 30 is in the sonic range and may further be in the range of about 80 Hz to about 500 Hz, for example. Moreover, the output amplitude of vibration may be in the range of about 0.05 mm to about 0.5 mm, and more specifically in the range of about 0.1 mm to about 0.5 mm, for example. In this regard, different output frequencies of vibration may be chosen by the user of the applicator 10 in order to accommodate different types of composite materials 12 e.g., composite materials having different types of thixotropic behavior.

The output frequency of vibration of tip is 20 is automatically adjusted by the controller 50 in response to a sensed condition of the composite material 12. To this end, the applicator 10 includes a sensor 60 operatively coupled to the controller 50 and located, in this embodiment, proximate the tip 20. The sensor 60 of this embodiment is configured to sense the viscosity of the composite material 12 during application of the composite material 12 onto the tooth 14. More specifically, in this embodiment, the sensor 60 is located proximate the base 27 of tip 20, and has a pair of schematically depicted sensing elements 60a, 60b within the elongated body 16. The first sensing element 60a is configured to sense a force exerted by the composite material 12 onto the tip 20 that is orthogonal (e.g., generally perpendicular) to the longitudinal axis 18. The second sensing element 60b is configured to sense a force exerted by the composite material 12 onto the tip 20 that is generally parallel to or along the longitudinal axis 18. Upon vibrating engagement of the tip 20 with the composite material 12, one or both of the sensing elements 60a, 60b deflect by an amount associated with a predetermined force exerted by the composite material 12 onto the tip 20. In use, the sensor 60 generates a signal to the controller 50 that corresponds to the sensed force and the controller 50 automatically varies the output frequency of vibrating apparatus 30 and thus, of tip 20, in response to the signal. Those of ordinary skill in the art will readily appreciate that sensor 60 may alternatively take other forms and/or be at a location different from that illustrated in the figures.

In a specific embodiment, the sensed force may be indicative of an increase in viscosity of the composite material 12. In such case, the controller 50 may respond to the sensed force by increasing the output frequency of tip 20, which in turn is effective to decrease the viscosity to a desired, predetermined level. In another specific embodiment, the sensed force may be indicative of a decrease in viscosity of the composite material 12, in which case the controller 50 may respond to the sensed force by decreasing the output frequency of tip 20. This decrease in output frequency, in turn, is effective to increase the viscosity of the composite material 12 to the desired, predetermined level. A desired, predetermined level of viscosity of composite material 12 may correspond to a sensed force, exerted on the tip 20, of about 0.2 N, for example. Such desired, predetermined level of viscosity may correspond to a viscosity level at which the shear stress of the material permits conventional composite materials 12 to be easily distributed on the tooth and less likely to adhere to the surface of the tip 20.

Figures 5, 6, 7:
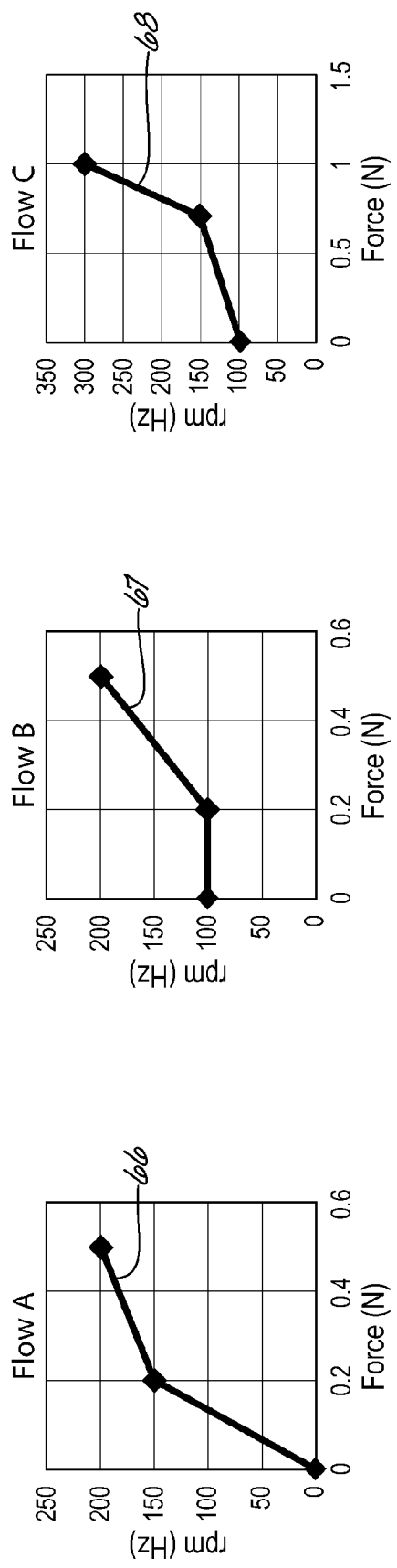
FIG. 5 is a graphical representation of one algorithm of operation of the applicator of FIGS. 1, 2, and 4.
FIG. 6 is a graphical representation of another algorithm of operation of the applicator of FIGS. 1, 2, and 4.
FIG. 7 is a graphical representation of yet another algorithm of operation of the applicator of FIGS. 1, 2, and 4.

With continued reference to FIGS. 1 and 4, and further referring to FIGS. 5-7, the applicator 10 may have several modes of operation, with each mode of operation being associated with one algorithm of operation of the controller 50, and each establishing a relationship between the sensed condition of the composite material 12 (e.g., the viscosity) and the output frequency. More specifically, the figures illustrate three different such algorithms 66, 67, 68 of operation, each relating the sensed force exerted by the composite material 12 on the tip 20 and the output frequency. In this regard, each of the algorithms 66, 67, 68 may correspond to a different type of composite material 12, such as a low-viscosity material, a high-viscosity material, a cement material for veneers or inserts, or a pit or fissure sealing material, for example.

In order to facilitate operation of applicator 10 in accordance with one of the algorithms 66, 67, 68, the applicator 10 is provided with a suitably located interface 70 (schematically depicted in the figures) permitting the user (e.g., dentist) to select among the several algorithms 66, 67, 68, for example, depending on the specific flow characteristics of the composite material 12 selected for the dental procedure. As illustrated in the exemplary algorithms 66, 67, 68, an output frequency in the range of about 100 Hz to about 150 Hz generally corresponds to a sensed force of 0.2 N, which in turn has been found, as discussed above, to correspond to a desirable level of viscosity and shear stress of the composite material 12. Operation of applicator 10 may thus involve automatically adjusting the output frequency based on the sensed force, so as to maintain a sensed force of about 0.2 N.

In use, one of the algorithms 66, 67, 68 may be chosen by the user. For example, the user may choose algorithm 68 (FIG. 7) for a specific type of composite material 12. As the applicator 10 engages the composite material 12 on the tooth 14, the force exerted by the composite material 12 onto the tip 20 is sensed by the sensor 60, which in turn generates a signal to the controller 50 indicative of the sensed force. If the sensed force is within an acceptable range (e.g., about 0.2 N) the controller 50 directs the vibrating apparatus 30 to continue to vibrate tip 20 with the same or similar output frequency and amplitude. If, on the other hand, the sensed force is indicative, for example, of an unacceptably high viscosity (e.g., the sensed force is higher than 0.2 N by more than a certain threshold), the controller 50, in response to the signal received from the sensor 60, directs the vibrating apparatus 30 to increase the output frequency until the viscosity of the material 12 decreases to a level corresponding to a sensed force of about 0.2 N.

For example, and with particular reference to FIG. 7, the sensed force may be about 0.7 N. In this regard, the controller 50 may direct the vibrating apparatus 30 to vibrate tip 20 with a frequency of about 110 Hz, for example, to thereby attain the target 0.2 N value of the sensed force, and which likely corresponds to a desired level of viscosity of the composite material 12. Conversely, if the sensed force is indicative, for example, of an unacceptably low viscosity (e.g., the sensed force is lower than 0.2 N by more than a certain threshold), the controller 50, in response to the signal received from the sensor 60, directs the vibrating apparatus 30 to decrease the output frequency of vibration of the tip 20 until the viscosity of the composite material 12 increases to a level corresponding to a sensed force of about 0.2 N.

In one aspect of this embodiment, the controller 50 may direct any adjustments in the output frequency to the vibrating apparatus 30 to be effected at an acceleration or deceleration rate that conforms with the expected behavior of the composite material 12, as predicted by the particular selected algorithm. Such controlled acceleration or deceleration may be desirable, for example, to prevent any overshoots or sudden drops in the viscosity of the composite material 12 as a result of an otherwise large increase or decrease of the output frequency over time.

While the invention has been illustrated by the description of one or more embodiments thereof, and while the embodiments have been described in considerable detail, they are not intended to restrict or in any way limit the scope of the invention to such detail. The various features shown and described herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope of the general inventive concept.

What is claimed is:

1. A vibrating applicator for applying a dental composite material onto a tooth, the applicator comprising:
    an elongated body;
    a tip coupled to said elongated body to apply the dental composite material onto the tooth;
    a vibrating apparatus for vibrating said tip;
    a sensor for sensing a condition of the dental composite material; and
    a controller operatively coupled to said vibrating apparatus and to said sensor and configured to automatically vary an output frequency of said vibrating apparatus in response to the condition sensed by said sensor,
    wherein said elongated body defines a longitudinal axis of the applicator, said sensor being configured to sense the condition in the form of a viscosity of the dental composite material by sensing a force exerted by the dental composite material on said tip in a direction orthogonal to said longitudinal axis.

2. The applicator of claim 1, wherein said controller is configured to decrease said output frequency in response to a sensed decrease in the force exerted by the dental composite material on said tip.

3. The applicator of claim 1, wherein said controller is configured to increase said output frequency in response to a sensed increase in the force exerted by the dental composite material on said tip.

4. A vibrating applicator for applying a dental composite material onto a tooth, the applicator comprising:
    an elongated body;
    a tip coupled to said elongated body to apply the dental composite material onto the tooth;
    a vibrating apparatus for vibrating said tip;
    a sensor for sensing a condition of the dental composite material; and
    a controller operatively coupled to said vibrating apparatus and to said sensor and configured to automatically vary an output frequency of said vibrating apparatus in response to the condition sensed by said sensor,
    wherein said elongated body defines a longitudinal axis of the applicator, said sensor being configured to sense the condition in the form of a viscosity of the dental composite material by sensing a force exerted by the dental composite material on said tip in a direction generally parallel to or along said longitudinal axis.

5. The applicator of claim 1, wherein said vibrating apparatus is operable to vibrate said tip with a frequency in the range of 80 Hz to 500 Hz.

6. The applicator of claim 1, wherein said vibrating apparatus is operable to vibrate said tip with an amplitude in the range of 0.1 mm to 0.5 mm.

7. The applicator of claim 1, wherein said tip is releasably coupled to said elongate body to thereby permit replacement thereof with another tip.

8. The applicator of claim 1, wherein said tip is generally spherical, said vibrating apparatus operable to vibrate said generally spherical tip with an output frequency in the range of 100 Hz to 500 Hz.

9. The applicator of claim 8, wherein said vibrating apparatus is operable to vibrate said generally spherical tip with an amplitude of 0.05 mm.

10. The applicator of claim 1, wherein said vibrating apparatus is powered by a battery, the applicator further comprising a compartment in said elongated body for receiving said battery.

11. The applicator of claim 1, wherein said tip includes one of a brush or a rotatable portion configured to distribute the dental composite material on the tooth during vibration of said tip.

12. The applicator of claim 1, wherein said controller has a plurality of predetermined algorithms of operation, each algorithm relating a physical property of a different dental composite material to said output frequency needed to maintain said physical property at a desired level, and wherein said controller is configured to receive the sensed condition from said sensor as an input of said physical property, and to adjust said output frequency in response thereto to maintain said desired level according to a selected one of the plurality of predetermined algorithms of operation.

13. A method for applying a dental composite material onto a tooth with an applicator having an applicator body, a tip coupled thereto for applying the dental composite material, a sensor within said applicator body capable of detecting conditions at the tip, and a vibrating apparatus for vibrating the tip, the method comprising:
    vibrating the tip with the vibrating apparatus while applying the dental composite material onto the tooth with the tip; and
    using the sensor to sense a viscosity of the dental composite material by sensing a force exerted by the dental composite material on the tip, wherein the applicator automatically varies an output frequency of the vibrating apparatus in response to the sensed viscosity of the dental composite material to viscosity the condition at a desired level.

14. The method of claim 13, further comprising:
    decreasing or increasing the output frequency, respectively, in response to a sensed decrease or increase in the sensed viscosity of the dental composite material.

15. The method of claim 13, further comprising:
    maintaining the output frequency such that it corresponds to a sensed force of 0.2 N.

16. The method of claim 13, further comprising:
    rotating a first portion of the tip relative to another portion thereof while vibrating the tip.

17. The method of claim 13, further comprising:
    vibrating the tip with a frequency in the range of about 80 Hz to 500 Hz.

18. The method of claim 13, further comprising:
    selecting among a plurality of algorithms of operation stored in an electronic memory of the applicator, each of the algorithms relating the sensed viscosity-to the output frequency needed to maintain the viscosity of the dental composite material at the desired level, wherein the applicator automatically varies the output frequency in accordance with the selected algorithm of operation.

19. A method for applying a dental composite material onto a tooth with an applicator having an applicator body, a tip coupled thereto for applying the dental composite material, a sensor within said applicator body capable of detecting conditions at the tip, and a vibrating apparatus for vibrating the tip, the method comprising:
vibrating the tip with the vibrating apparatus while applying the dental composite material onto the tooth with the tip; and
using the sensor to sense a viscosity of the dental composite material by sensing a force exerted by the dental composite material on the tip, wherein the applicator automatically controls the vibrating apparatus in response to the sensed viscosity of the dental composite material.

20. The applicator of claim 4, wherein said controller is configured to decrease said output frequency in response to a sensed decrease in the force exerted by the dental composite material on said tip.

21. The applicator of claim 4, wherein said controller is configured to increase said output frequency in response to a sensed increase in the force exerted by the dental composite material on said tip.

22. The applicator of claim 4, wherein said vibrating apparatus is operable to vibrate said tip with a frequency in the range of about 80 Hz to 500 Hz.

23. The applicator of claim 4, wherein said vibrating apparatus is operable to vibrate said tip with an amplitude in the range of 0.1 mm to 0.5 mm.

24. The applicator of claim 4, wherein said tip is releasably coupled to said elongate body to thereby permit replacement thereof with another tip.

25. The applicator of claim 4, wherein said tip is generally spherical, said vibrating apparatus operable to vibrate said generally spherical tip with an output frequency in the range of 100 Hz to 500 Hz and an amplitude of 0.05 mm.

26. The applicator of claim 4, wherein said tip includes one of a brush or a rotatable portion configured to distribute the dental composite material on the tooth during vibration of said tip.

27. The applicator of claim 4, wherein said controller has a plurality of predetermined algorithms of operation, each algorithm relating a physical property of a different dental composite material to said output frequency needed to maintain said physical property at a desired level, and wherein said controller is configured to receive the sensed condition from said sensor as an input of said physical property, and to adjust said output frequency in response thereto to maintain said desired level according to a selected one of the plurality of predetermined algorithms of operation.

* * * * *

UNITED STATES PATENT AND TRADEMARK OFFICE
CERTIFICATE OF CORRECTION

PATENT NO. : 9,452,027 B2  Page 1 of 1
APPLICATION NO. : 12/634986
DATED : September 27, 2016
INVENTOR(S) : Beat Kilcher et al.

It is certified that error appears in the above-identified patent and that said Letters Patent is hereby corrected as shown below:

In the Specification

In Column 5, Line 22, "vibration of tip is 20 is" should read --vibration of tip 20 is--.

In the Claims

In Column 8, Line 50, Claim 13, "material to viscosity the condition at a desired level." should read --material to maintain the viscosity at a desired level.--.

In Column 9, Line 1, Claim 18, "sensed viscosity-to the" should read --sensed viscosity to the--.

In Column 10, Line 3, Claim 22, "the range of about 80 Hz" should read --the range of 80 Hz--.

Signed and Sealed this
Second Day of May, 2017

Michelle K. Lee
*Director of the United States Patent and Trademark Office*